United States Patent [19]
Laukaitis

[11] Patent Number: 5,173,750
[45] Date of Patent: Dec. 22, 1992

[54] REFLECTION DENSITOMETER

[75] Inventor: Joseph F. Laukaitis, Rochester, N.Y.

[73] Assignee: Eastman Kodak Company, Rochester, N.Y.

[21] Appl. No.: 475,575

[22] Filed: Feb. 6, 1990

[51] Int. Cl.⁵ .............................................. G01N 21/55
[52] U.S. Cl. ................................ 356/445; 250/214 B; 307/311
[58] Field of Search ............... 356/445, 446, 432, 448, 356/447, 323, 325; 250/252.1, 353, 341, 358.1, 359.1, 360.1, 214 B, 214 A, 221, 222.1; 355/14 D; 307/311

[56] References Cited

U.S. PATENT DOCUMENTS 4,553,033 10/1985 Hubble, III et al. ................. 356/445
4,851,689 7/1989 Hasegawa ....................... 250/214 B Primary Examiner—Vincent P. McGraw
Assistant Examiner—LaCharles P. Keesee, II
Attorney, Agent, or Firm—David A. Howley

[57] ABSTRACT

A reflection densitometer includes a light source and a photodetector having an output which has a signal component characteristic of the amount of reflected light received from a surface to be measured and a noise component. The noise component of the output is isolated in time by switching the light source on and off so as to create alternating first and second time periods during which the output of the photodetector is characteristic of only the noise component and in which the output of the photodetector is characteristic of both the signal component plus the noise component, respectively. The output of the photodetector during the second time period is subtracted from the output during the first time period to obtain a signal characteristic of only the output of the photodetector characteristic of relected light received. The signal is held constant during the first and second periods by a sample and hold circuit adapted to sample the signal during the second periods and to hold the sampled signal during the first periods.

11 Claims, 2 Drawing Sheets

REFLECTION DENSITOMETER

BACKGROUND OF THE INVENTION

TECHNICAL FIELD

This invention relates generally to infrared reflection densitometers for measuring the relative optical density of a developed toner image on a test patch for controlling process parameters in an electrostatographic machine.

BACKGROUND ART

In electrostatographic machines such as printers and copiers, control of process parameters is required to produce images having constant and predeterminable densities. Such parameters include electrical charger energization, exposure energy, development bias voltage, toner concentration, and image transfer potential.

One method of monitoring the process parameters is to measure the developed toner mass on an image receiver; and a technique for measuring the developed toner mass is to measure the reflective optical density of an exposed and developed area, called a patch, on the image receiver.

Known techniques for measuring the relative optical density of the developed toner image include the use of infrared reflectance densitometers. In U.S. Pat. Nos. 4,550,254 and No. 4,553,033, several stages of a photodiode circuit monitors and controls the light output from a light emitting diode, detects undesirable scattered background light from the image receiver, and detects the light reflected from the developed toner image. An automatic gain control circuit adjusts the output gain of the reflection densitometer, and a sample and hold circuit adjusts for different effects of aging, current leakage, or other circuit component performance characteristics.

The system described in these prior art patents forces the output of the photodiode circuit to zero reference when there is no light input. The correction for changing electronic factors is achieved by comparing the output of the photodiodes when the light emitting diodes are off to a voltage of a reference generator, and then subtracting it from the measured density value.

DISCLOSURE OF INVENTION

It is an object of the present invention to provide a reflection densitometer which does not require the calibration step, or the attending circuit complexities, of the prior art systems.

According to one aspect of the present invention, A densitometer includes a light source positioned to project light rays toward a surface whose reflectance is to be measured. A photodetector is positioned to receive light rays reflected from the surface, and has an output which is characteristic of the amount of reflected light received plus a noise component. The output of the photodetector characteristic of only the noise component is isolated in time from the output of the photodetector characteristic of reflected light received plus the noise component.

According to a preferred feature of the present invention, the output of the photodetector which is characteristic of reflected light received plus the noise component is subtracted from the output of the photodetector which is characteristic of only the noise component to obtain a densitometer output signal characteristic of only the output of the photodetector characteristic of reflected light received.

According to another preferred feature of the present invention, the light source is switched on and off so as to create alternating first and second time periods in which the output of the photodetector is characteristic of only the noise component and in which the output of the photodetector characteristic of reflected light received plus a noise component, respectively.

According to yet another feature of the present invention, the densitometer output signal is held constant during the first and second periods by a sample and hold circuit adapted to sample during the second periods and to hold the sample during the first periods.

The invention, and its objects and advantages, will become more apparent in the detailed description of the preferred embodiments presented below.

BRIEF DESCRIPTION OF THE DRAWINGS

In the detailed description of the preferred embodiments of the invention presented below, reference is made to the accompanying drawings, in which.

BEST MODE FOR CARRYING OUT THE INVENTION

Figure 1:
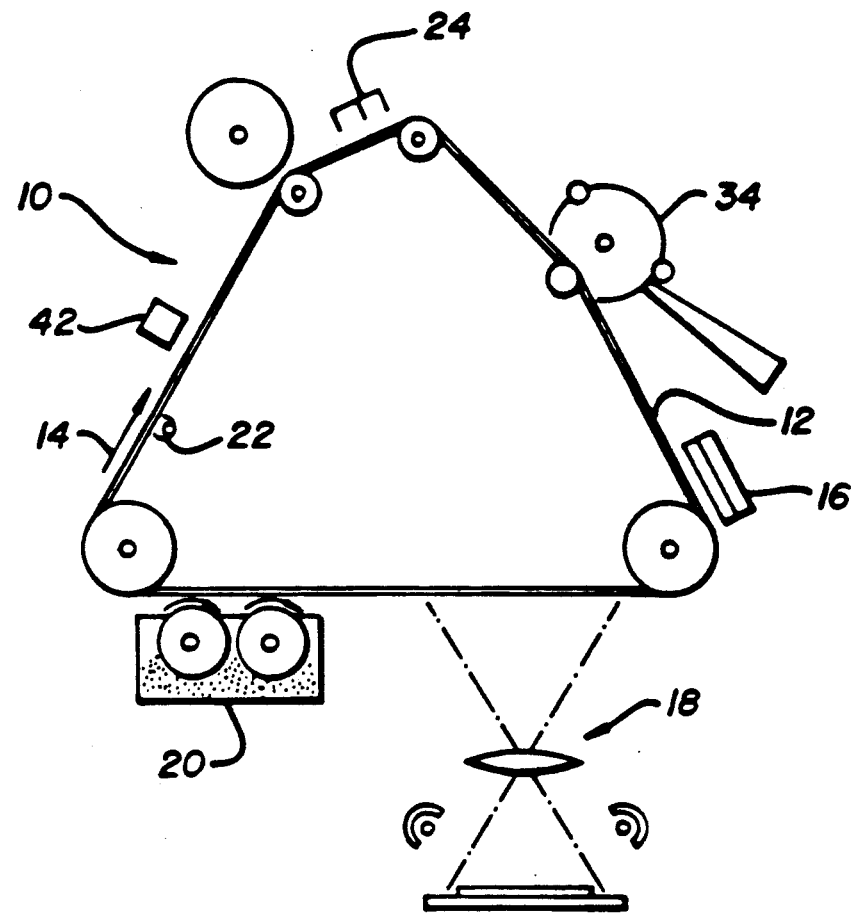
FIG. 1 is a vertical schematic representation of an electrostatographic machine with which the present invention is usable.

FIG. 1 shows an electrophotographic machine 10 having an image receiver in the form of a photoconductive belt 12 which moves in a clockwise direction, as represented by an arrow 14.

An electrostatic charge is applied to belt 12 at a charging station 16. Images are projected onto belt 12 at an exposure station 18, providing a suitable interframe distance between image areas. The projected light images dissipate the electrostatic charge at the exposed areas of the photoconductive belt to form a latent electrostatic image on belt 12.

The latent electrostatic image on belt 12 is developed with toner at a developer station 20. The toner image is then subjected to radiation by a post-development erase lamp 22 to reduce the electrical stress on photoconductive belt 12 and to reduce the attraction between the toner image and belt 12.

As the toner image on belt 12 approaches a transfer station 24, a copy sheet is fed from a supply (not shown). Transfer station 24 serves as a means to effect the movement of the toner image to copy sheets (not shown) by applying a charge opposite in polarity to that of the toner image and neutralizing the charge on the copy sheet so that it easily separates from belt 12. The copy sheet bearing toner is then passed through a pair of heated fuser rollers (not shown). Mechanical and electrical cleaning of photoconductive belt 12 is effected at a cleaning station 34.

Figure 2:
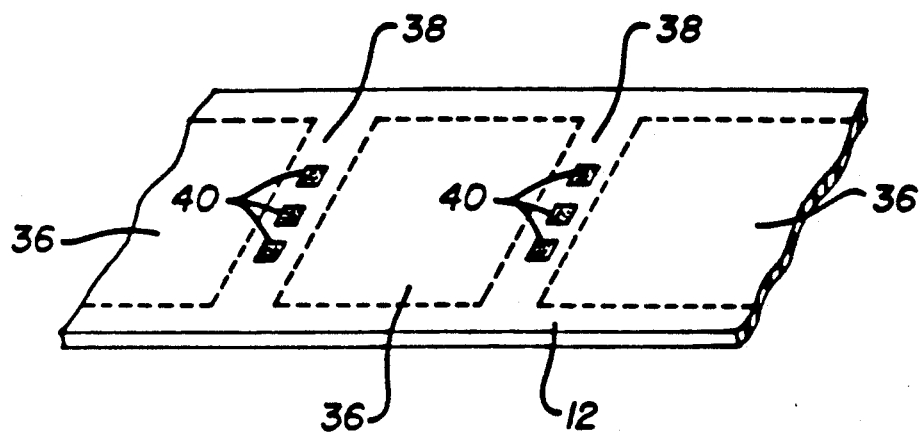
FIG. 2 is an enlarged fragmentary perspective view of a portion of the electrostatographic machine of FIG. 1.

Referring to FIG. 2, photoconductive belt 12 is illustrated with a plurality of image areas or film frames 36 spaced slightly apart from each other along the longitudinal length of the belt; thus defining non-image interframe regions 38.

In order to control the electrographic process, it is known to provide one or more test patches 40 of toner in interframe regions 38. The test patches can be formed by leaving such areas charged when the other parts of the photoconductive belt outside image areas 36 are discharged, and then exposing the area to a predetermined level of irradiation. Then toner is applied to the test patches by development station 20 of FIG. 1. In this manner the density of toner on the test patches is directly related to the density of toner in image areas 36. By way of example, three toned test patches 40 are shown adjacent to each other in each interframe region 38. However, more or fewer test patches could be provided if desired. When multiple est patches for each interframe region are used for density measurement, the patches preferably are exposed to obtain different density levels of toner so that the electrographic process can be checked and controlled for various operating parameters.

Referring back to FIG. 1, as test patches 40 pass a reflection densitometer 42, light rays from a light emitting diode reflect from the surface of each test patch to an associated photodetector. A signal generated by densitometer 42 is provided to a logic and control unit (not shown) which is programmed to provide various control signals to portions of the apparatus in response to the signal received from the densitometer. For example, the control signal from the densitometer can cause the logic and control unit to regulate a number of process parameters such as the voltage applied to photoconductive belt 12 at charging station 16, the intensity or duration of exposure at station 18, the bias voltage of development station 20, and/or the concentration of toner in the developer mixture. In general, the signal from densitometer 42 can be used to control any process parameter that effects the density of the toner images on the photoconductor.

Figure 3:
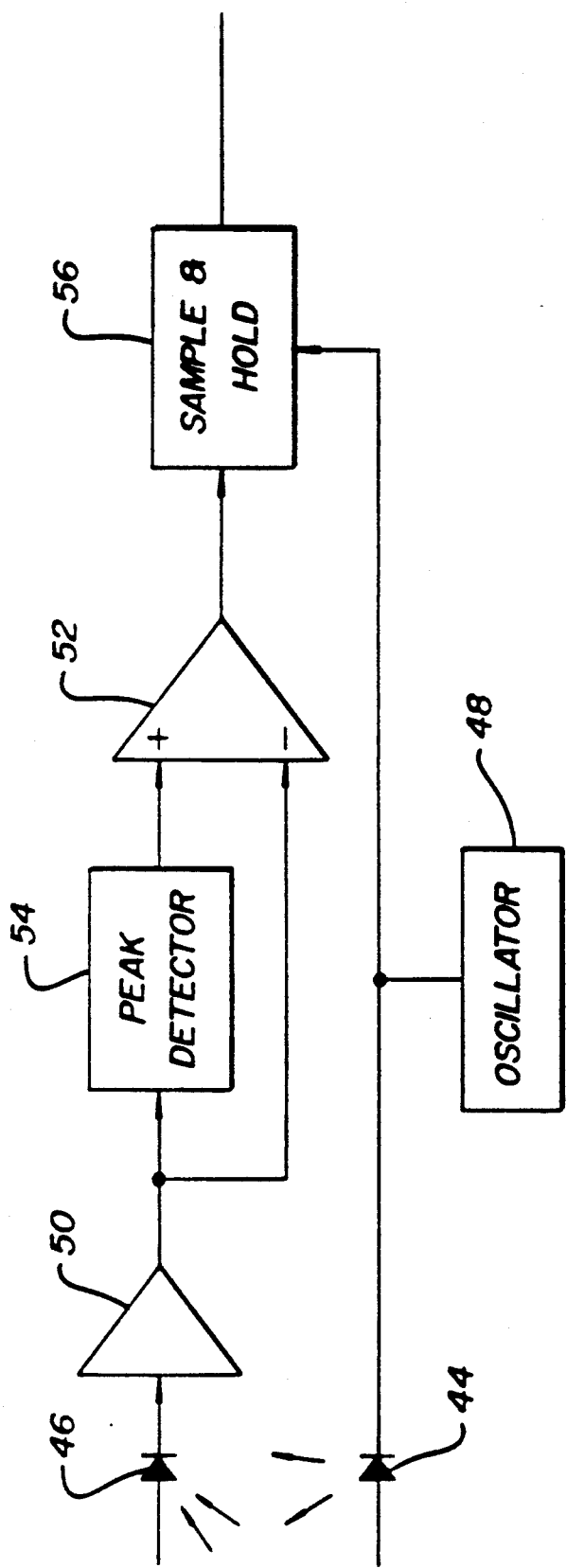
FIG. 3 is a schematic of a densitometer circuit of the machine of FIGS. 1 and 2.

FIG. 3 is a schematic of the circuit of densitometer 42 of FIG. 1. A light emitting diode 44 is aligned with a photodetector 46 such that the photodiode collects at least a portion of the radiation from the light emitting diode which is reflected from the surface of photoconductive belt 12 of FIG. 1. Photodetectors generally have a so called dark current, and mag respond to a certain quantity of undesirable background or stray light. Therefore, the signal from photodetector 46 includes an output component which is characteristic of the amount of reflected light received, and a noise component. The present invention provides a novel way to distinguish the two.

The light emitting diode is switched on and off by an oscillator 48. The frequency of the oscillator is chosen to correspond to the response of photodetector 46, and that of a logarithmic amplifier 50 which compresses the photodetector output signal, say 100:1. As an example, oscillator 48 may have a frequency of, say, one kHz.

Figure 4B:
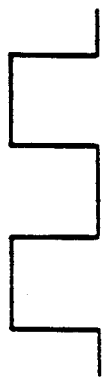
FIGS. 4a and 4b are signal output wave form of various component of the circuit of FIG. 3.
Figure 4A:

The signal output of logarithmic amplifier 50 is shown in FIG. 4a. Note that logarithmic amplifier 50 inverts the signal, so the top of the wave form represents the output of photodetector 46 when light emitting diode 44 is turned off (the dark level), and the bottom of the wave form represents the output of photodetector 46 when light emitting diode 44 is turned on.

The output of logarithmic amplifier 50 is inputted to the negative terminal of a difference amplifier 52, as well as to a peak detector 54. The peak detector has a relatively long time constant so as to hold the dark level voltage output of logarithmic amplifier 50, which drifts very slowly.

The output of peak detector 54 is inputted to the positive terminal of difference amplifier 52 as a reference such that the input to a sample and hold circuit 56 is an amplified difference between the dark level peak voltage and the sampled density signals. The input to the sample and hold circuit is a square wave shown in FIG. 4b, the top of which represents the sample density.

Sample and hold circuit 56 is simply a peak detector with a time constant switched by oscillator 48 so that the frequency of light emitting diode 44 is the same as that of the sample and hold circuit. Accordingly, the output signal of the sample and hold circuit represents only the radiation reflected from the photoconductive belt surface with no component of background light or dark current. This signal can be used by the machine process control.

The invention has been described in detail with particular reference to preferred embodiments thereof, but it will be understood that variations and modifications can be effected within the spirit and scope of the invention.

What is claimed is:

1. A densitometer for measuring the reflectance of a surface, said densitometer comprising:
    a light source positioned to project light rays toward a surface whose reflectance is to be measured;
    a photodetector positioned to receive light rays reflected from the surface, said photodector having an output which has a signal component characteristic of the amount of reflected light received and a noise component;
    a logarithmic amplifier for amplifying the output of said photodector;
    means for detecting a logarithmically amplified output of said photodector having only a noise component and a logarithmically amplified output of said photodector having said signal component plus a noise component; and
    means for subtracting the logarithmically amplified output of said photodector having only a noise component from the logarithmically amplified output of said photodetector having said signal component plus a noise component to obtain a signal substantially characteristic of reflected light received by said photodector.

2. A densitometer for measuring the reflectance of a surface, said densitometer comprising:
    a light source positioned to project light rays toward a surface whose reflectance is to be measured;
    a photodetector positioned to receive light rays reflected from the surface, said photodector having an output which has a signal component characteristic of the amount of reflected light received and a noise component;
    a logarithmic amplifier for amplifying the output of said photodetector;
    means for switching said light source off and on so as to create alternating first and second time periods in which the output of said photodetector is characteristic of only a noise component and in which the output of said photodetector is characteristic of both said signal component plus a noise component, respectively; and
    means for subtracting a logarithmically amplified output of said photodetector detected during said second period from an amplified output of said logarithmic amplifier during said first period to obtain a signal substantially characteristic of reflected light received by said photodetector.

3. A densitometer as defined in claim 2 further comprising means for holding said signal constant during said first and second periods.

4. A densitometer as defined in claim 3 wherein said holding means is a sample and hold circuit adapted to sample said signal during said second periods and to hold the sampled signal during said first periods.

5. A densitometer as defined in claim 3 wherein said holding means is a sample and hold circuit, and further comprising means, associated with said switching means for activating said sample and hold circuit to sample said signal during said second periods and to hold the sampled signal during said first periods.

6. A densitometer for measuring relative optical densities of a developed toner image on the surface of an image receiver, said densitometer comprising:

a light emitting diode positioned to project light rays toward a developed toner image on the image on the surface of an image receiver;

a photodiode positioned to receive light rays reflected from the toner image, said photodiode having an output which has a signal component characteristic of the amount of reflected light received and a noise component;

a logarithmic amplifier for amplifying the output of said photodiode;

means for switching said light emitting diode off and on so as to create alternating first and second time periods in which the output of said photodiode is characteristic of only the noise component and in which the output of said photodiode is characteristic of both said signal component plus a noise component, respectively; and means for subtracting a logarithmically amplified output of said photodiode detected during said second period from a logarithmically amplified output of said photodiode detected during said first period to obtain a signal substantially characteristic of reflected light received by said photodiode.

7. A densitometer as defined in claim 6 wherein said subtracting means comprises:

a peak detector for outputting a signal characteristic of the noise component from the output of said photodiode; and a difference amplifier for subtracting the output of said photodiode from the output of said peak detector.

8. A densitometer as defined in claim 6 further comprising means for holding said signal constant during said first and second periods.

9. A densitometer as defined in claim 8 wherein said holding means is a sample and hold circuit adapted to sample said signal during said second periods and to hold the sampled signal during said first periods.

10. A densitometer as defined in claim 8 wherein said holding means is a sample and hold circuit, and further comprising means, associated with said switching means for activating said sample and hold circuit to sample said signal during said second periods and to hold the sampled signal during said first periods.

11. A densitometer as defined in claim 6 wherein said switching means is an oscillator coupled to said light emitting diode and said sample and hold circuit.

* * * * *